(12) United States Patent
Schneider-Nieskens

(10) Patent No.: US 7,347,871 B2
(45) Date of Patent: Mar. 25, 2008

(54) BREAST PROSTHESIS

(75) Inventor: Reinhold Schneider-Nieskens, Celle (DE)

(73) Assignee: THAMERT Orthopadische Hifsmittel GmbH & Co. KG, Burgwedel (DE)

( * ) Notice: Subject to any disclaimer, the term of this patent is extended or adjusted under 35 U.S.C. 154(b) by 140 days.

(21) Appl. No.: 11/064,800

(22) Filed: Feb. 24, 2005

(65) Prior Publication Data

US 2005/0197698 A1    Sep. 8, 2005

(30) Foreign Application Priority Data

Mar. 3, 2004   (DE) .................. 20 2004 003 278

(51) Int. Cl.
*A61F 2/121* (2006.01)
*A41C 3/10* (2006.01)

(52) U.S. Cl. ............................. 623/7; 450/38

(58) Field of Classification Search ............... 623/7–8; 450/38

See application file for complete search history.

(56) References Cited

U.S. PATENT DOCUMENTS

| 3,494,365 A | | 2/1970 | Beals | |
|---|---|---|---|---|
| 4,125,117 A | * | 11/1978 | Lee | 450/57 |
| 4,955,907 A | * | 9/1990 | Ledergerber | 623/8 |
| 6,080,037 A | * | 6/2000 | Lee et al. | 450/38 |
| 6,228,116 B1 | * | 5/2001 | Ledergerber | 623/8 |
| 6,811,463 B2 | * | 11/2004 | Martz | 450/57 |
| 2003/0163197 A1 | | 8/2003 | Chen | |

FOREIGN PATENT DOCUMENTS

| DE | 7449175 U | 5/1975 |
|---|---|---|
| DE | 2912120 A1 | 10/1980 |
| DE | 29712015 U1 | 11/1998 |
| EP | 0320590 B2 | 10/1988 |
| EP | 0657148 A1 | 2/1994 |

* cited by examiner

*Primary Examiner*—Suzette Gherbi
(74) *Attorney, Agent, or Firm*—Martin Faier; James M. Faier; Faier & Faier P.C.

(57) ABSTRACT

A breast prosthesis fabricated from silicone and characterized by an outer shell shaped region and an inner shall-shaped region wherein the inner region is profiled in the form of rings arranged concentrically around the mamilla. The rings may be formed bellows-like adapted to be pushed toward one another when pressure is exerted on the prosthesis. Annularly shaped recesses and beads may be arranged between the rings. The inner region may consist of lower density silicone gel having a firmness of lower penetration value but firmer than the outer region. Preferably, the outer region is slightly thicker above the manilla than below the manilla, and may have a third shell shaped region arranged between the outer and inner shell shaped regions. A recess can be provided in the lower part of the prosthesis to define an air cushion for permitting silent release of air from the prosthesis responsive to pressure applied against the prosthesis.

16 Claims, 2 Drawing Sheets

BREAST PROSTHESIS

The invention pertains to a breast prosthesis, in particular, of silicone with an outer shell-shaped region and an inner shell-shaped region, wherein the inner region and the outer region have the form of a product that has different properties.

BACKGROUND AND SUMMARY OF THE INVENTION

A breast prosthesis of the initially mentioned type is known, for example, from EP 0 320 590 B2. In this known breast prosthesis, an outer body has a hardness that matches the soft, elastic resilience of the natural breast tissue while an inner body or inner region has a firmer consistency such that it can adapt to the scar region.

The invention is based on the objective of developing a breast prosthesis of the initially mentioned type that has particularly favorable dimensional and deformation properties and can have a particularly lightweight structure.

This objective is attained with a breast prosthesis have the characteristics the present invention. Advantageous additional developments of the invention are also disclosed in this application.

In a breast prosthesis, in particular, of silicone with an inner shell-shaped region and an outer shell-shaped region which have different and novel properties, the invention provides a second region that is arranged within the outer region in the form of a profiled ring structure. The design in the form of such a profiled structure makes it possible to increase the mechanical stability of the prosthesis. Consequently, it is possible to utilize lighter materials. In addition, a particularly desirable effect with respect to the shape and the deformation of the prosthesis can be achieved with such a special profiling.

The profiled structure has the form of a ring structure, particularly a concentric ring structure. In this case, the rings preferably are concentrically arranged around the mamilla. In other preferred embodiments, a special rib or bead geometry is utilized which increases the stability of the breast prosthesis similar to a ribbing in lightweight building components.

In one preferred embodiment, the inner profiled region comprises at least two peripheral rings, and preferably three peripheral rings. These rings may also have the form of a bead-like fashion such that they can be pushed into one another like a bellows when pressure is exerted upon a point of the prosthesis. These rings are preferably interrupted and spaced apart from one another. In one particularly preferred embodiment, the interruption of the rings extends horizontally through the mamilla. It is also preferred to provide a vertically extending interruption of the rings, wherein this interruption extends, in particular, vertically through the mamilla and only interrupts the central and the inner ring. Additionally or alternatively to an interruption of the central ring, one or more interruptions are preferably provided in the lower half of the breast prosthesis, wherein these interruptions preferably are respectively aligned at an of angle of about 45°, with reference to the vertical line. Due to this measure, the prosthesis adapts itself to a brassiere cup similar to a natural breast. When pressure is exerted upon the point of the prosthesis, the concentric ribs or beads have a bellows-like compression of the prosthesis material. This enables the breast prosthesis to flatten when the wearer lies on her back. The breast prosthesis is also able to flatten during physical contact with another person.

According to another preferred additional development of the invention, nominal folding recesses are provided in the breast prosthesis. These recesses are preferably arranged between the beads and have an annular shape.

In another preferred additional development of the invention, the inner shell-shaped region consists of a lightweight silicone. The lightweight silicone is preferably produced by embedding very small hollow spheres in the silicone gel such that the resulting lightweight silicone has a much lower density than normal silicone gel. This results in a reduction of the total weight of the prosthesis. The design of the breast prosthesis according to the invention still provides a sufficient stability. The inner region preferably consists of a silicone that is particularly firm in comparison with conventional lightweight silicone prostheses. The firmness of the inner region is adjusted, in particular, such that it has a penetration value of approximately 180. The outer layer, in contrast, is preferably manufactured from normal silicone or normal silicone gel that preferably is relatively soft in comparison with conventional silicone materials used for this purpose and has a penetration value, in particular, of approximately 260. The outer region consequently is thus formed softer than the inner region.

In another preferred embodiment of the invention, the outer shell-shaped region has a form slightly thicker above the mamilla than below the mamilla. The ratio between the thickness of the outer region above the mamilla and the thickness below the mamilla preferably lies at approximately 1.5. According to another additional development of the invention, the breast prosthesis may have the form of a three-chamber prosthesis, wherein a third shell-shaped region preferably is arranged between the outer region and the inner region.

In another preferred embodiment of the invention, the breast prosthesis is provided with a recess in its lower region. An air cushion enclosed with the prosthesis can escape through this recess without developing any noise when pressure is exerted upon the prosthesis.

The invention is described in detail below with reference to one preferred embodiment that is illustrated in the figures. The schematic figures show:

DESCRIPTION OF PREFERRED EMBODIMENTS

Figure 1:
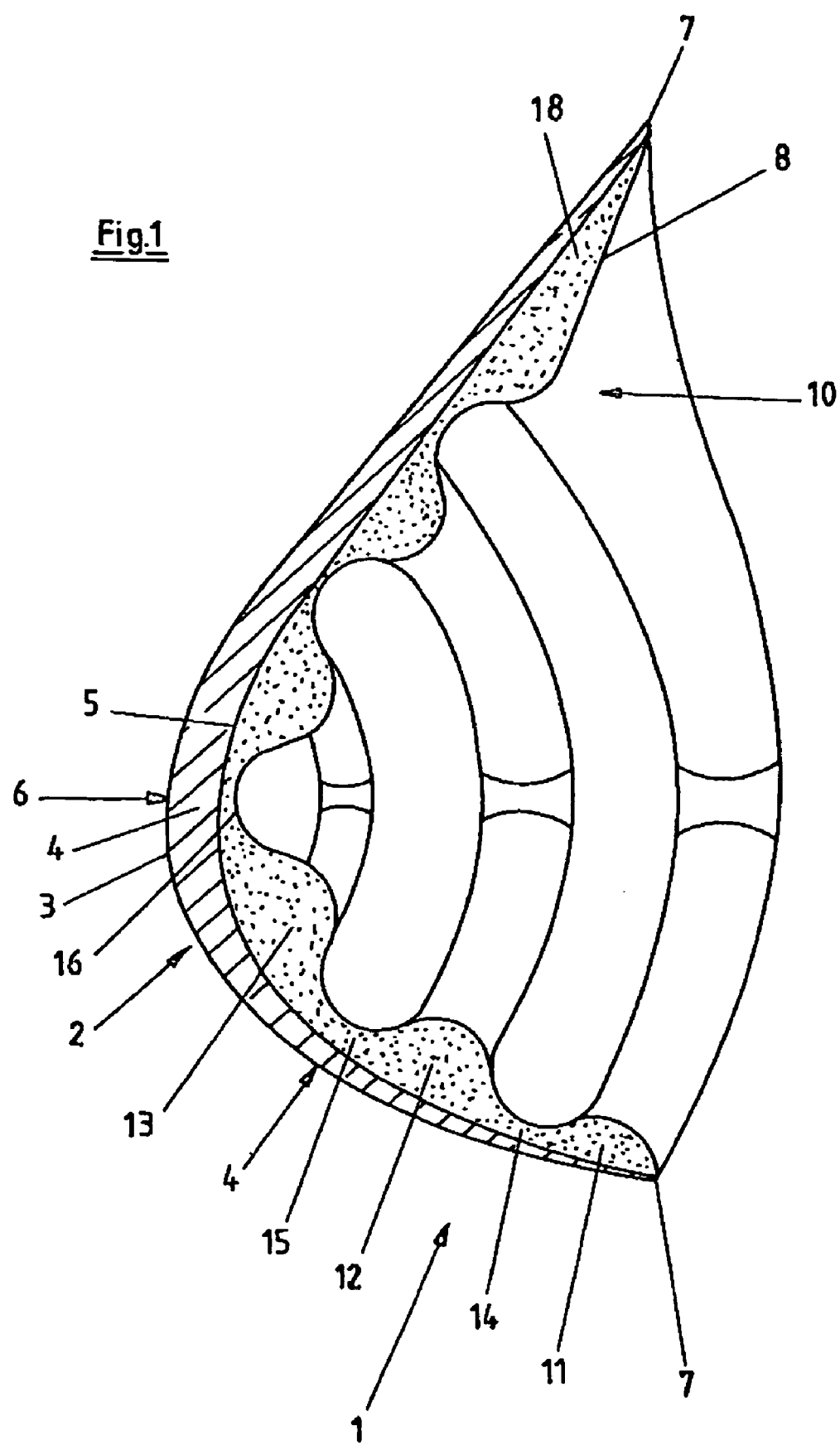
FIG. 1 is a vertical section through a breast prosthesis according to the invention.

FIG. 1 shows a vertical section through the breast prosthesis 1 with the shell-shaped outer region 2 and the shell-shaped inner region 10. The outer region 1 represents the externally visible side of the breast prosthesis 1. A silicone gel layer 4 is accommodated in a cover layer or sheath that is formed by an outer layer 3 and an inner layer 5, either or both of which may be fabricated from plastics, such as polyurethane, between which the silicone gel layer 4 is situated.

This silicone gel layer consists of a very soft silicone gel with a penetration value of approximately 260. The silicone gel layer of the outer region 2 is not constant, but made thicker above the mamilla 6 than below the mamilla 6. The thickness ratio (thickness above mamilla to thickness below mamilla) lies at approximately 1.5 in this case. The layers 3 and 5 lie on top of one another and are welded together in a peripheral end region 7. A third cover layer 8 that forms the lower end of the inner shell-shaped region 10 accommodated between the layer 5 and the layer 8 is also welded into this end region 7. This shell-shaped region 10 that faces the inner side is made in a profiled fashion. This structure is achieved by utilizing a correspondingly profiled moulding tool that is inserted into the breast prosthesis from inside during the vulcanization of the silicone.

The inner shell-shaped region 10 is made with concentric rings or beads 11, 12 and 13 in this case. Annular regions with a thinner material thickness 14 and 15 lie between the beads 11, 12, and 13, and are also referred to as nominal folding recesses. The moulding body that provides the inner region with this profiled structure preferably has radii in the region of the beads 11, 12 and 13 that are identical to those in the region of the recesses 14 and 15 lying between the beads. This means that the beads 11, 12, and 13 and recesses 14 and 15 correspond to one another with respect to their dimensions.

In the region of the mamilla 6, the inner shell-shaped region 10 is realized with a very thin central region 16. The bead 13 concentrically extends around this region 16, wherein said bead is followed by the peripheral depression or recess 15, a bead 12, a depression or nominal folding recess 14 and another bead or ring 11. The outermost ring or bead 11 is in a form which is particularly wide and flattened toward the outer edge 17 such that a very good contact between the breast prosthesis 1 and the skin of wearer is achieved at this location. In an upper section 18, the outer bead 11, particularly the edge 17, is realized in an elongated, pointed fashion such that a particularly favorable contact can be achieved in this region. A recess 19 is provided in the rings or beads 11, 12 and 13 in the inner shell-shaped region 10 that faces the body, namely such that it extends horizontally through the region 16, i.e., the region of the mamilla.

Figure 2:
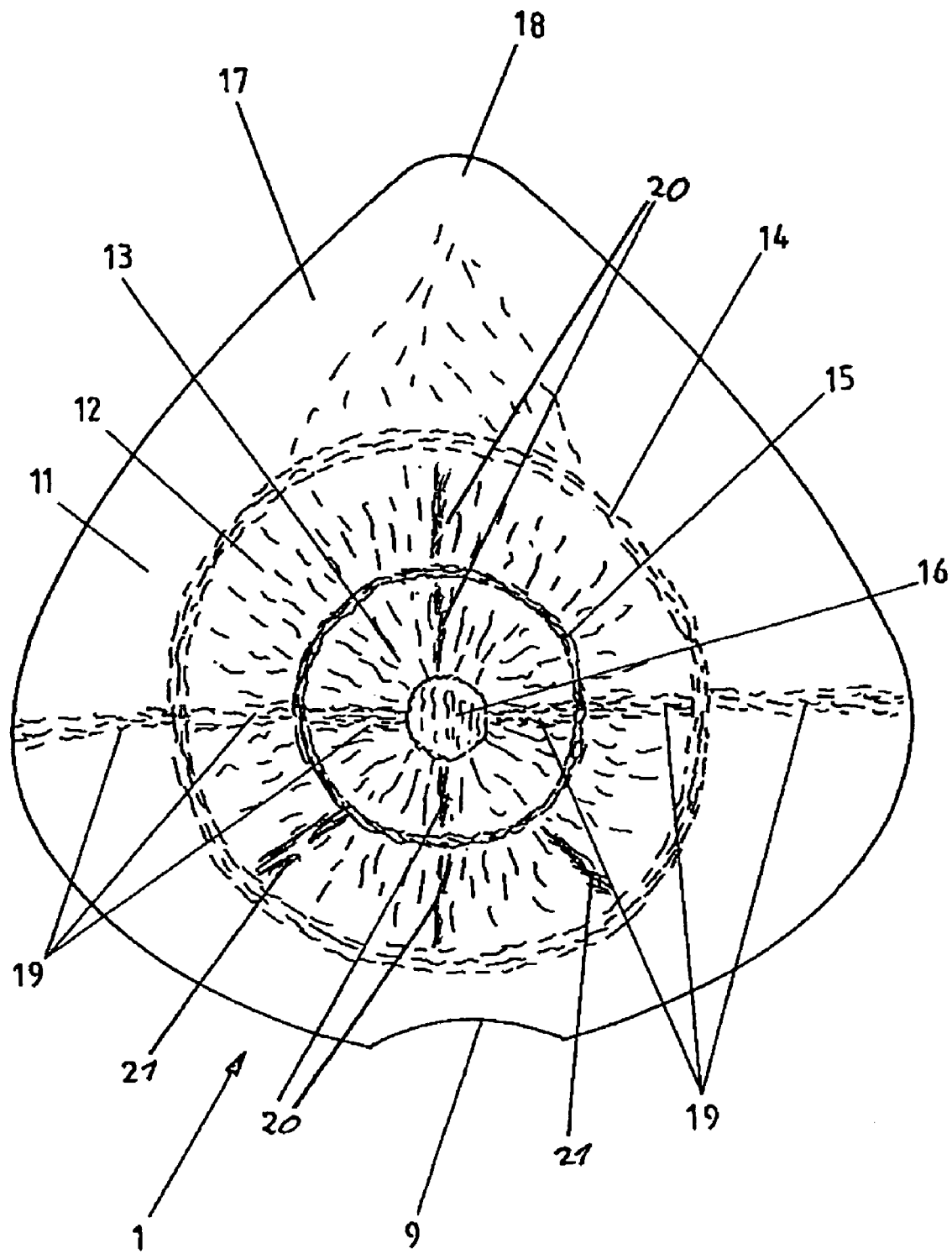
FIG. 2 is a rear view of the breast prosthesis according to the invention.

FIG. 2 shows a rear view of the breast prosthesis 1, i.e., the side that faces the body. The inner shell-shaped region 10 of the prosthesis 1 is illustrated particularly well in this figure. This figure also shows the particularly thin central region 16 of the mamilla as well as the other peripheral recesses 14 and 15 and the rings 11, 12 and 13. The interruption 19 of the rings 11, 12 and 13 that horizontally extends over the entire breast prosthesis is also illustrated very well in this figure. In addition, interruptions 20 of the rings preferably are also provided, particularly of the rings 12 and 13, i.e., the central ring and the inner ring. These interruptions vertically extend through the breast prosthesis as well as the mamilla. Interruptions 21 preferably also provided.

These interruptions preferably are only arranged in the central ring 12 and respectively aligned at an angle of about 45° with reference to the vertical line, i.e., to the interruptions 20, wherein these interruptions preferably are only provided in the lower half of the breast prosthesis. A recess 9 is provided in the lower end region of the breast prosthesis 1. This recess 9 is created in a semicircular fashion and interrupts the edge 17 that adjoins the body. This structure form air cushion having a envelop permitting air to escape through the recess without developing any noise, and, also, any enclosed water is able to drain out through the recess after swimming.

While preferred embodiments have been described in considerable detail, it should be understood that many changes and modifications in the structures disclosed may be made without departing from the spirit or scope of the invention and it is intended that the invention should not be limited to the exact structure disclosed.

The invention claimed is:

1. In a silicone breast prosthesis to be worn external to the user, said prosthesis having a mamilla and an outer shell shaped region and an inner shell shaped region, wherein said inner region is profiled in the form of rings arranged concentrically around said mamilla, wherein said inner region consists of lower density silicone gel having a firmness of lower penetration value but firmer than said outer region.

2. The breast prosthesis according to claim 1, characterized in that said inner region profiled rings comprise at least two peripheral rings.

3. The breast prosthesis according to claim 2, characterized in that an interruption is provided between said rings.

4. A breast prosthesis to be worn external to the user, said prosthesis consisting of silicone with an outer shell-shaped region and an inner shell-shaped region, wherein the inner region and the outer region have a form which is characterized in an arrangement where said inner region within said outer region has the form of a profiled ring structure, wherein said outer region consists of a soft silicone that has a penetration value, in particular, of approximately 260 as compared to said inner region and said outer region is softer that said inner region.

5. The breast prosthesis according to claim 4, characterized in that said inner region contains nominal folding recesses.

6. The breast prosthesis according to claim 4, characterized in that said inner region consists of lightweight silicone.

7. The breast prosthesis according to claim 4, characterized in that said inner region consists of a firm silicone that has a penetration value of approximately 180, as compared to said outer region.

8. The breast prosthesis according to claim 7, characterized in that said outer region consists of normal silicone.

9. The breast prosthesis according to claim 4, said prosthesis having a mamilla formed therein and characterized in that said outer region is slightly thicker above said mamilla than below said mamilla.

10. In a breast prosthesis to be worn external to the user, said prosthesis having a mamilla and an outer shell shaped region and an inner shell shaped region, wherein said inner region is profiled in the form of rings arranged concentrically around said mamilla, wherein said rings are formed bellow-like and are adapted to be pushed toward one another when pressure is exerted on said prosthesis.

11. The breast prosthesis according to claim 10, having a lower end region and characterized in that said breast prosthesis contains a recess in said lower end region.

12. The breast prosthesis according to claim 11, wherein said recess defines an air cushion.

13. The breast prosthesis according to claim 10, wherein beads are arranged between said rings.

14. The breast prosthesis according to claim 10, wherein recesses are formed in said inner shell region making said inner region less dense than said outer region.

15. The breast prosthesis according to claim 14, wherein a third shell shaped region is arranged adjacent said inner recess and remote from an outer recess.

16. The breast prosthesis according to claim 10, wherein a layer of covering separates said regions.

* * * * *